United States Patent [19]
Drew et al.

[11] Patent Number: 5,496,398
[45] Date of Patent: Mar. 5, 1996

[54] REDUCTION OF MICROORGANISMS IN KAOLIN CLAY SLURRIES

[75] Inventors: Sharon M. Drew; Jeffrey C. Bruns, both of Sandersville; Jessica E. Kogel, Milledgeville, all of Ga.

[73] Assignee: Thiele Kaolin Company, Sandersville, Ga.

[21] Appl. No.: 331,323

[22] Filed: Oct. 28, 1994

[51] Int. Cl.$^6$ .................. A61L 2/02; A61L 2/16
[52] U.S. Cl. .................. 106/15.05; 106/18.33; 210/764; 422/28; 501/148
[58] Field of Search .................. 106/15.05, 18.32, 106/18.33; 209/3; 210/764; 422/28; 423/327.1; 514/301, 372, 373, 724; 501/148

[56] References Cited

U.S. PATENT DOCUMENTS

| | | | |
|---|---|---|---|
| 4,330,562 | 5/1982 | Nassar | 426/310 |
| 4,781,298 | 11/1988 | Hemstock et al. | 209/3 |
| 4,975,109 | 12/1990 | Friedman, Jr. et al. | 71/67 |
| 4,997,550 | 3/1991 | Cobb et al. | 209/166 |
| 5,026,564 | 6/1991 | Hayden | 426/237 |
| 5,049,400 | 9/1991 | Hayden | 426/237 |
| 5,322,834 | 6/1994 | Hsu | 504/156 |

OTHER PUBLICATIONS

*The Control of Microbiological Growth in Slurry Kaolin*, Brochure from ECC International, publication date unknown.
*The Lester Process for Sanitation*, Bulletin 52291 from Lester Technologies, publication date believed to be 1991 [No Month].
*AMA-415*, Material Safety Data Sheet from Vinings Industries, May 1, 1990.
*AMA-35D-P*, Material Safety Data Sheet from Vinings Industries, May 1, 1990.
*UCARCIDE Antimicrobial 750*, Material Safety Data Sheet from Union Carbide, Sep., 1986.
*PROXEL GXL*, Material Safety Data Sheet from ICI Americas; TKC-R-00042-A, Jul. 14, 1986.

Primary Examiner—Anthony Green
Attorney, Agent, or Firm—Jones & Askew

[57] ABSTRACT

A biologically stable kaolin clay slurry is manufactured by heating a kaolin clay slurry for at least 15 minutes at a temperature of at least 93° C., cooling the slurry to a temperature no greater than about 35° C. and then adding a microbiocide to the slurry.

9 Claims, No Drawings

REDUCTION OF MICROORGANISMS IN KAOLIN CLAY SLURRIES

TECHNICAL FIELD

This invention relates to a process for the reduction of microorganisms in kaolin clay slurries. In a more specific aspect, this invention relates to a process for the treatment of kaolin clay slurries by a combination of low temperature heat and reduced levels of a microbiocidal agent, which yields kaolin clay slurries having substantially reduced microbial contamination and, therefore, greater utility. This invention also relates to kaolin clay slurries produced by the process of this invention.

BACKGROUND OF THE INVENTION

Kaolin is a naturally occurring, relatively fine, white clay which may be generally described as a hydrated aluminum silicate. Kaolin clay is widely used as a filler and pigment in various materials, such as rubber and resins, and in various coatings, such as paints and coatings for paper.

Slurries of kaolin clay are generally made by mixing a quantity of kaolin clay with water and other optional additives. However, chemicals added during beneficiation to achieve various desired results in these slurries, such as dispersants, colloidal thickeners, ammonia and leaching chemicals, also may provide usable energy sources for aerobic and anaerobic microbial growth. Because of these additives, most commercial kaolin slurries are susceptible to microbial spoilage and, therefore, require high levels of microbiocides to control aerobic and anaerobic microbial growth. Examples of such microorganisms include algae, bacteria, mold, spores, etc. The growth of microorganisms and their by-products tends to adversely affect the properties of a kaolin clay slurry by altering the color, odor and viscosity of the slurry. In many instances, the altered slurry may have little or no commercial value.

The problem of such microbial contamination in kaolin clay slurries is similar to problems in other industries, such as the pulp and paper industry or the petroleum industry, which have aqueous sources that encourage microbial growth. Microbial contamination can also significantly affect the efficiency of industrial structures or processes such as cooling towers or lubricating systems. Because of these problems, microbiocidal agents (i.e., microbiocides) are conventionally used, often at very high dosages, to eliminate or reduce the growth of microorganisms.

Microbiocides are well-known agents for the control of microbial growth in aqueous systems, such as kaolin clay slurries. However, the use of such agents raises environmental concerns which influence the choice of a microbiocide. Many of the early microbiocides were chlorinated or mercurial compounds which left harmful by-products in the environment. Some of the formerly used compounds, such as formaldehyde, are no longer environmentally acceptable because these compounds were found to be carcinogenic or teratogenic. These problems, therefore, limit the number of microbiocides available for use to those microbiocides which are less effective and more expensive.

There are a variety of problems associated with the use of microbiocides in the kaolin clay industry. These problems include the environmental impact associated with many microbiocides, the high cost of microbiocides and the large amounts of microbiocides that may be necessary to reach the desired microbial control level in a specific situation.

Microbiocides which are commonly used in kaolin clay slurries include 1,5-pentanediol; tetrahydro-3-5-dimethyl-2H-1,3,5 -thiadiazine-2-thione; 1,2-benzisothiazolin-3-one; and 5-chloro-2-methyl- 4-isothiazolin-3-one/2-methyl-4-isothiazolin-3-one. The disadvantages to the use of these microbiocides include the high cost of their use at the necessary higher dosages, their ineffectiveness in certain slurries and their environmental impact.

As previously indicated, slurries of kaolin clay differ widely in their susceptibility to microbial contamination. Process additives are key factors but other factors, such as the degree of mechanical or chemical processing, variations in crude clay sources, differences in crude clay particle size distributions and crude clay impurities, may also create additional problems.

A method to solve some of the problems associated with microbial contamination is disclosed in Friedman et al. U.S. Pat. No. 4,975,109, which provides for using a combination of chemicals to act in a synergistic fashion to kill microorganisms. However, this patent requires the addition of an oxidizing agent, a microbiocide, a surfactant and an anti-corrosive material.

For various reasons, the prior art fails to provide an acceptable process that will control the level of microbial activity in a variety of kaolin clay slurries without the cost related to high dosages of the combinations of chemicals. Therefore, a need exists in the kaolin clay industry for an effective and broadly applicable process to reduce microbial growth and, therefore, provide commercially useful kaolin clay slurries having greater utility (i.e., a longer shelf life).

SUMMARY OF THE INVENTION

Briefly described, the present invention provides a biologically stable kaolin clay slurry for various purposes. More specifically, this invention provides a process for treatment of kaolin clay slurries to reduce microbial contamination while also significantly reducing the amount of microbiocide necessary for such treatment of the slurries.

The process of this invention may be broadly described as the low temperature heat treatment of a kaolin clay slurry, followed by addition of a microbiocide in substantially reduced amounts than are required without heat treatment to reach the same level of microbial control.

The combination of these two steps is critical. We have found that neither treatment alone, low temperature heat or reduced amount of microbiocide, provides the same level of microbial control as does the combination.

The present invention provides a kaolin clay slurry that has an extended shelf life over the time period normally encountered in this industry, thus maintaining the utility of the slurry for various purposes.

Additionally, the kaolin clay slurry produced by this invention can be treated at less expense because of the substantially reduced amount of microbiocide that is added to control the microbial contamination.

Accordingly, an object of this invention is to provide a process for the reduction of microorganisms in kaolin clay slurries.

Another object of this invention is to provide a process for the reduction of microorganisms in kaolin clay slurries to produce slurries having a longer period of utility.

Another object of this invention is to provide a process which is effective in controlling the growth of aerobic microorganisms in a kaolin clay slurry.

Another object of this invention is to provide a process which is effective in controlling the growth of anaerobic microorganisms in a kaolin clay slurry.

Another object of this invention is to provide a process for the treatment of kaolin clay slurries by low temperature heat, which allows the subsequent addition of significantly reduced amounts of microbiocide than is necessary without such heat treatment.

Another object of this invention is to provide a process for the heat treatment of kaolin clay slurries, which allows the subsequent addition of significantly reduced amounts of microbiocides, thus providing a more environmentally and economically beneficial process than current methods.

Another object of this invention is to provide a process for the heat treatment of kaolin clay slurries, followed by addition of a microbiocide, that will maintain control of microbial growth.

These and other objects, features and advantages of this invention will become apparent from the following detailed description.

DETAILED DESCRIPTION OF THE INVENTION

In accordance with the present invention, kaolin clay slurries are treated sequentially by low temperature heat, followed by addition of a microbiocide.

In this invention, we have discovered that a heat treatment of kaolin clay slurries, at temperatures of at least about 93° C., followed by addition of a microbiocide, provides enhanced microbial control that is not found with either heat treatment or microbiocidal treatment alone.

We believe that the initial heat treatment is effective in eliminating a majority of the microorganisms present in the slurry, while the subsequent addition of a microbiocide is effective in controlling the growth of microorganisms which remain in the slurry or which contaminate the slurry at a later time.

In the first stage of this process, the kaolin clay slurry is treated with heat. The kaolin clay slurry is subjected to moist heat treatment at a temperature of at least 93° C. in equipment that is standard for the kaolin clay industry, such as a Parr pressure reactor, for at least 15 minutes. After moist heat treatment, the kaolin clay slurry is cooled to a temperature no greater than about 35° C.

The heat treatment step required by this invention can be effectively accomplished using heat generated by microwaves, steam, heated coils, heat exchanger, jacketed reactor, etc.

The second stage of this process involves addition of a microbiocide to the cooled slurry. The amount of microbiocide added to the slurry is at least 20 ppm (weight of microbiocide as received to total slurry weight). The microbiocides added can be selected from conventional microbiocides, such as 1,5-pentanediol (sold by Union Carbide Corp. under the trademark Ucarcide); 1,2-benzisothiazolin-3-one (sold by Zeneca Inc. under the trademark Proxel); 5-chloro-2 -methyl-4-isothiazolin-3-one/2-methyl-4-isothiazolin-3-one (sold by Vinings Industries under the trademark AMA-415); tetrahydro-3,5-dimethyl-2H-1,3,5-thiadiazine-2-thione (sold by Vinings Industries under the trademark AMA-35D); or other commercially available microbiocides.

With the process of this invention, kaolin clay slurries can be obtained which have less than 1,000 colony forming units per milliliter (CFUs/ml.) after 14 days of aging and, after 30 days of aging, also have less than 1,000 colony forming units per milliliter. Additionally, the process of this invention can be used to produce kaolin clay slurries which meet the more stringent specifications of a customer.

The present invention is further illustrated by the following examples which are illustrative of certain embodiments designed to teach those of ordinary skill in this art how to practice this invention and to represent the best mode contemplated for carrying out this invention.

Data Interpretation

With regard to the following examples, data interpretation may sometimes be complicated by a number of factors, including microbial growth cycles and microbiocidal mode of action. Microorganisms undergo a period of adjustment to their environment (in this invention, a kaolin clay slurry) prior to the onset of cell division. This period of adjustment is referred to as the lag phase, during which the cells are increasing in size and in metabolic activity.

Once the period of adjustment is completed, the lag phase comes to an end and the cells begin to replicate. During this exponential phase, an exponential increase in cell numbers occurs. A semilogarithmic plot of the population growth at this time is linear, with the slope reflecting the generation time of the growing microorganisms. After this period of growth, the rate of increasing cell numbers decreases. Populations are still increasing in total number, but not as rapidly. During this phase, as the essential nutrients begin to be depleted, the accumulation of end products may create a toxic environment detrimental to growth, and the growth and reproductive rates decrease. For a period of time, known as the stationary phase, them is either a slow increase or no net change in cell numbers; the number of cells dividing is matched by the number of cells dying. Many of the cells are not growing, but are in a state of maintenance. The overall metabolic activity becomes sluggish. As the growth rate continues to decrease, and death rates continue to increase, the population enters the decline phase. The rate of decline varies among species of microorganisms, but is most often, very rapid among bacterial species (i.e., a few days).

A quantitative plate count is used to measure microbial populations. The microbial culture is quantitatively diluted, appropriate dilutions are pipetted into a sterile Petri plate, and liquid tempered agar medium is poured into the plate and mixed with the culture by swirling. The plates are incubated for 48 hours at 37° C. Each isolated cell capable of growth on the agar medium produces a macroscopic colony. The number of colonies developing on the agar plate multiplied by the quantitative dilution of the sample provides an approximation of the number of viable cells in the original sample, and is reported as colony forming units per milliliter of slurry (CFUs/ml).

The differences in population size during the growth phases are reflected in the plate count data, as seen in Table 1, Control Sample. This sample data shows increases in population size through 14 days, followed by a subsequent steady decline.

Another factor which can sometimes complicate data interpretation is the microbiocidal mode of action (i.e., the specific killing action involved). As can be seen in Tables 4–5, the Ucarcide biocide provides a quick killing action by crosslinking the microbial cells; the cells die quickly due to the inability to intake oxygen or other nutrients, or to output waste products. The Proxel and AMA-415 biocides, however, have a different killing action. These biocides act on the metabolic pathways of the microbial cell. Eventually, the ability for nutrient uptake, energy production and respiration are inactivated. This process may take as long as 1 week to begin killing the microorganisms (reference. Table 3, AMA-415 dosages; Note: In these two samples, the microbiocide levels present are unable to preserve the slurry samples long-term).

is either 200 ppm or 400 ppm. The kaolin clay slurry samples are stored at 37° C. for 30 days and tested at various time intervals for microbial contamination. The results of these tests are in Table 1.

TABLE 1

| Time | Control - No Heat No Biocide | Example 1 Heat Only 104° C. | Example 2 Proxel 50 ppm 104° C. | Example 3 Proxel 100 ppm 104° C. | Example 4 AMA415 200 ppm 104° C. | Example 5 AMA415 400 ppm 104° C. |
|---|---|---|---|---|---|---|
| 1 hour | | | | | | |
| aerobe | 10,000 | * | * | * | * | <1 |
| anaerobe | 1 | * | * | * | * | ** |
| Day 1 | 15,300 | * | * | * | * | * |
| | 1 | * | * | * | * | * |
| Day 2 | 23,800 | 105 | * | * | * | * |
| | 1 | * | * | * | * | * |
| Day 3 | 24,700 | 168 | * | * | <1 | * |
| | 1 | * | * | * | * | * |
| Day 7 | TNTC | 1600 | <1 | * | * | <1 |
| | 1 | * | * | * | * | * |
| Day 14 | TNTC | 154 | * | <1 | * | <1 |
| | 1 | * | * | * | * | * |
| Day 21 | 2,400 | 106 | * | 3 | * | * |
| | 1 | * | * | * | * | * |
| Day 27 | 420 | 910 | * | 3 | * | * |
| | 1 | * | * | * | * | * |
| Day 30 | 300 | 300 | <1 | <1 | * | * |
| | * | * | * | * | * | * |

TNTC = Too Numerous To Count (i.e., more than 30 million)
*No microorganisms are detected.
Note:
Aerobic and anaerobic counts (× 10³ CFUs/ml.)

For published references which further discuss data interpretation, see *Laboratory Experiments in Microbiology.* Case, C., Johnson, T. R.; Benjamin/Cummings Publishing Company, 1984; *Laboratory Exercises in Microbiology.* 6th Edition. Wistreich, G. A. Lechtman, M. D.; Macmillan Publishing Company, 1988; and *The Microbes.* VanDemark, P. J., Batzing, B. L.; Benjamin/Cummings Publishing Company, 1987.

The following examples also confirm that this invention is applicable to, and effective with, a variety of kaolin clays. More specifically, these clays include those sold by Thiele Kaolin Company under the trademarks Kaobrite 90—a high brightness No. 2 coating clay; Kaofine—a standard No. 1 fine particle size coating clay; and Kaogloss-a standard No. 1 coating clay.

Examples 1–5

A kaolin clay slurry, marketed by Thiele Kaolin Company under the trademark Kaobrite 90, fully dispersed at 60% solids with no biocide added, is obtained. The slurry is aged until counts of >3×10⁷ aerobic microorganisms and >1×10³ anaerobic microorganisms are obtained.

The kaolin clay slurry is divided into test samples of 3 gallons each and heated for 15 minutes, at 15 psi pressure, at 104° C. The slurry samples are cooled to 35° C. by an ice bath.

When the slurry has cooled to 35° C., the microbiocide of choice is immediately added. The amount of Proxel added is either 50 ppm or 100 ppm. The amount of AMA-415 added Examples 6–10

A kaolin clay slurry, marketed by Thiele Kaolin Company under the trademark Kaobrite 90, fully dispersed at 60% solids with no biocide added, is obtained, as in Examples 1–5. The slurry is aged until counts of >3×10⁷ aerobic microorganisms and >1×10³ anaerobic microorganisms are obtained.

The kaolin clay slurry is divided into test samples of 3 gallons each and heated for 15 minutes, at 15 psi pressure, at 121 ° C. The slurry samples are cooled to 35° C. by an ice bath.

When the slurry has cooled to 35° C., the microbiocide is immediately added. The amount of Proxel added is either 50 ppm or 100 ppm as shown in Table 2. The amount of AMA-415 added is either 200 ppm or 400 ppm as shown in Table 2. The kaolin clay slurry samples are stored at 37° C. for 30 days and tested at various time intervals for microorganism contamination. The results of these tests are shown in Table 2.

TABLE 2

| Time | Control - No Heat No Biocide | Example 6 Heat Only 121° C. | Example 7 Proxel 50 ppm 121° C. | Example 8 Proxel 100 ppm 121° C. | Example 9 AMA415 200 ppm 121° C. | Example 10 AMA415 400 ppm 121° C. |
|---|---|---|---|---|---|---|
| 1 hour | | | | | | |
| aerobe | 10,000 | * | * | <1 | * | * |
| anaerobe | 1 | * | * | * | * | * |
| Day 1 | 15,300 | 4.3 | * | * | * | * |
|  | 1 | * | * | * | * | * |
| Day 2 | 23,800 | 460 | * | * | * | * |
|  | 1 | * | * | * | * | * |
| Day 3 | 24,700 | 130 | <1 | <1 | <1 | <1 |
|  | 1 | * | * | * | * | * |
| Day 7 | TNTC | 1280 | <1 | <1 | * | <1 |
|  | 1 | * | * | * | * | * |
| Day 14 | TNTC | 1070 | <1 | * | * | * |
|  | 1 | * | * | * | * | * |
| Day 21 | 2,400 | 1790 | * | * | * | * |
|  | 1 | * | * | * | * | * |
| Day 27 | 420 | 98 | * | * | * | * |
|  | 1 | * | * | * | * | * |
| Day 30 | 300 | 120 | * | * | * | * |
|  | * | * | * | * | * | * |

TNTC = Too Numerous To Count (i.e., more than 30 million)
*No microorganisms are detected.
Note:
Aerobic and anaerobic counts ($\times 10^3$ CFUs/ml.)

Examples 11–14

The procedure of Examples 6–10 is followed, except that the samples are not subjected to a heat treatment. The results of these tests, with biocide only, are shown in Table 3.

At the identical concentrations of the same microbiocides, there is more undesirable microbial activity than when the microbiocide is combined with treatment of the kaolin clay with moist heat in accordance with this invention.

TABLE 3

| Time | Control - No Heat No Biocide | Example 11 Proxel 50 ppm No Heat | Example 12 Proxel 100 ppm No Heat | Example 13 AMA415 200 ppm No Heat | Example 14 AMA415 400 ppm No Heat |
|---|---|---|---|---|---|
| 1 hour | | | | | |
| aerobe | 10,000 | 5,400 | 190 | 147 | 58 |
| anaerobe | 1 | * | * | * | * |
| Day 1 | 15,300 | 1310 | 81 | 123 | 98 |
|  | 1 | * | * | * | * |
| Day 2 | 23,800 | 153 | 30 | 14.4 | 6.0 |
|  | 1 | * | * | * | * |
| Day 3 | 24,700 | 110 | 11.9 | 13.0 | 4.9 |
|  | 1 | * | * | * | * |
| Day 7 | TNTC | 12 | 108 | 10.7 | 3.1 |
|  | 1 | * | * | * | * |
| Day 14 | TNTC | 108 | 8.2 | <1 | <1 |
|  | 1 | * | * | * | * |
| Day 21 | 2,400 | 131 | 4.9 | 3.0 | 1.5 |
|  | 1 | * | * | * | * |
| Day 27 | 420 | 164 | 3.0 | 3.0 | 18.1 |
|  | 1 | * | * | * | * |
| Day 30 | 300 | 168 | 4.4 | 4.0 | 115 |
|  | * | * | * | * | * |

TNTC = Too Numerous To Count (i.e., more than 30 million)
*No microorganisms are detected.
Note:
Aerobic and anaerobic counts ($\times 10^3$ CFUs/ml.)

Examples 15–20

A kaolin clay slurry, marketed by Thiele Kaolin Company under the trademark Kaogloss, fully dispersed at 58% solids with no biocide added, is obtained. The slurry is aged for several days to establish bacteria growth.

The kaolin clay slurry is divided into test samples of 3 gallons each, and the samples are heated in a Parr reactor, at 15 psi pressure, for 15 minutes at either 93° C. or 104° C. After heating, the samples are cooled to 35° C.

After the samples cool to 35° C., the microbiocide of choice is immediately added. The amount of Ucarcide added is either 100 ppm or 300 ppm (wet weight: wet weight basis).

The samples are then stored at 37° C. in an environmental chamber for 30 days and tested at various time intervals for microbial contamination. The results of these tests are shown in Tables 4 and 5.

TABLE 4

| Time | Control - No Heat No Biocide | Example 15 Heat Only 93° C. | Example 16 Ucarcide 100 PPM 93° C. | Example 17 Ucarcide 300 PPM 93° C. |
|---|---|---|---|---|
| 1 Hour | | | | |
| aerobe | 5500 | 500 | * | * |
| anaerobe | >1 | * | * | * |
| 24 Hours | 28000 | 1030 | * | * |
|  | >1 | * | * | * |
| 48 Hours | TNTC | 1480 | * | * |
|  | >10000 | * | * | * |
| 72 Hours | TNTC | 1680 | * | * |
|  | >10000 | * | * | * |
| 7 Days | TNTC | 2040 | * | 0.1 |
|  | >10000 | * | * | * |
| 14 Days | TNTC | 2250 | * | * |
|  | >10000 | * | * | * |

TABLE 4-continued

|  | Control - No Heat No Biocide | Example 15 Heat Only 93° C. | Example 16 Ucarcide 100 PPM 93° C. | Example 17 Ucarcide 300 PPM 93° C. |
|---|---|---|---|---|
| Time |  |  |  |  |
| 21 Days | TNTC | 6600 | >1 | * |
|  | >10000 | * | * | * |
| 27 Days | TNTC | 23100 | * | * |
|  | >10000 | * | * | * |
| 30 Days | TNTC | 25400 | * | * |
|  | >10000 | * | * | * |

TNTC = Too Numerous To Count (i.e., more than 30 million)
*No microorganisms are detected.
Note:
Aerobic and anaerobic counts (× $10^3$ CFUs/ml.)

TABLE 5

| Time | Control - No Heat No Biocide | Example 18 Heat Only 104° C. | Example 19 Ucarcide 100 PPM 104° C. | Example 20 Ucarcide 300 PPM 104° C. |
|---|---|---|---|---|
| 1 Hour |  |  |  |  |
| aerobe | 5500 | 270 | * | * |
| anaerobe | >1 | * | * | * |
| 24 Hours | 28000 | 980 | 0.2 | 0.1 |
|  | >1 | * | * | * |
| 48 Hours | TNTC | 2410 | * | * |
|  | >10000 | * | * | * |
| 72 Hours | TNTC | 2730 | * | * |
|  | >10000 | * | * | * |
| 7 Days | TNTC | 2910 | * | * |
|  | >10000 | * | * | * |
| 14 Days | TNTC | 3000 | * | * |
|  | >10000 | * | * | * |
| 21 Days | TNTC | 2590 | * | * |
|  | >10000 | * | * | * |
| 27 Days | TNTC | 14200 | * | * |
|  | >10000 | * | * | * |
| 30 Days | TNTC | 13000 | * | * |
|  | >10000 | * | * | * |

TNTC = Too Numerous To Count (i.e., more than 30 million)
*No microorganisms are detected.
Note:
Aerobic and anaerobic counts (× $10^3$ CFUs/ml.)

Examples 21–26

A kaolin clay slurry, marketed by Thiele Kaolin Company under the trademark Kaofine, fully dispersed at 60% solids with no biocide added, is obtained. The slurry is aged for several days to establish bacteria growth.

The kaolin clay slurry is divided into test samples of 3 gallons each, and the samples are heated in a Parr reactor, at 15 psi pressure, for 15 minutes at either 104° C. or 121° C. After heating, the samples are cooled to 35° C.

After the samples cool to 35° C., the microbiocide of choice is immediately added. The amount of AMA-35D added is 20 ppm (wet weight: wet weight basis). The amount of Proxel added is either 25 or 100 ppm (wet weight: wet weight basis).

The samples are then stored at 37° C. in an environmental chamber for 30 days and tested at various time intervals for microbial contamination. The results of these tests are shown in Tables 6 and 7.

TABLE 6

| Time | Control - Heat Only 104° C. | Example 21 AMA-35D 20 ppm 104° C. | Example 22 Proxel 25 ppm 104° C. | Example 23 Proxel 100 ppm 104° C. |
|---|---|---|---|---|
| 1 Hour |  |  |  |  |
| aerobe | 1.9 | 2.0 | * | 4.0 |
| anaerobe | * | * | * | * |
| 24 Hours | 3.0 | 2.0 | 1.0 | 5.0 |
|  | * | * | * | * |
| 48 Hours | 77 | * | * | * |
|  | * | * | * | * |
| 72 Hours | 1140 | * | * | * |
|  | * | * | * | * |
| 7 Days | 3700 | * | * | * |
|  | * | * | * | * |
| 14 Days | 5300 | * | * | * |
|  | * | * | * | * |
| 21 Days | 7100 | * | 3.0 | 1.0 |
|  | * | * | * | * |
| 27 Days | TNTC | * | * | * |
|  | * | * | * | * |
| 30 Days | TNTC | * | * | * |
|  | * | * | * | * |

TNTC = Too Numerous To Count (i.e., more than 30 million)
*No microorganisms are detected.
Note:
Aerobic and anaerobic counts (× $10^3$ CFUs/ml.)

TABLE 7

| Time | Control - Heat Only 121° C. | Example 21 AMA-35D 20 ppm 121° C. | Example 22 Proxel 25 ppm 121° C. | Example 23 Proxel 100 ppm 121° C. |
|---|---|---|---|---|
| 1 Hour |  |  |  |  |
| aerobe | * | * | 2.0 | * |
| anaerobe | * | * | * | * |
| 24 Hours | * | * | 1.0 | * |
|  | * | * | * | * |
| 48 Hours | * | * | * | * |
|  | * | * | * | * |
| 72 Hours | 30 | * | * | * |
|  | * | * | * | * |
| 7 Days | 33 | * | * | * |
|  | * | * | * | * |
| 14 Days | 78 | * | * | * |
|  | * | * | * | * |
| 21 Days | 6900 | * | 3.0 | 1.0 |
|  | * | * | * | * |
| 27 Days | 1250 | * | * | * |
|  | * | * | * | * |
| 30 Days | 2100 | * | 3.0 | * |
|  | * | * | * | * |

TNTC = Too Numerous To Count (i.e., more than 30 million)
*No microorganisms are detected.
Note:
Aerobic and anaerobic counts (× $10^3$ CFUs/ml.)

This invention has been described in detail with particular reference to certain embodiments, but variation and modifications can be made without departing from the spirit and scope of the invention as defined in the following claims.

What is claimed is:

1. A process to reduce microorganisms in a kaolin clay slurry, wherein the process comprises the sequential steps of:
   a. heating the slurry for at least 15 minutes at a temperature of at least 93° C.;
   b. cooling the heated slurry to a temperature no greater than about 35° C.; and c. adding a microbiocide to the cooled slurry, wherein the amount of microbiocide added is at least 20 ppm, based on the weight of commercial microbiocide product to total slurry weight.

2. A process as defined by claim 1 wherein the temperature used in heating the kaolin clay slurry is from 93° C. to 220° C.

3. A process as defined by claim 1 wherein the temperature used in heating the kaolin clay slurry is at least 104° C.

4. A process as defined by claim 1 wherein the temperature used in heating the kaolin clay slurry is at least 121° C.

5. A process as defined by claim 1 wherein the microbiocide is 1,5-pentanediol; tetrahydro-3,5-dimethyl-2H-1,3,5-thiadiazine-2-thione; 1,2-benzisothiazolin-3-one; 5-chloro-2-methyl-4-isothiazolin-3-one/2-methyl-4-isothiazolin-3-one; or a mixture thereof.

6. A process as defined in claim 1 wherein the microbiocide is 1,5-pentanediol.

7. A process as defined in claim 1 wherein the microbiocide is tetrahydro-3,5-dimethyl-2H-1,3,5-thiadiazine-2-thione.

8. A process as defined in claim 1 wherein the microbiocide is 1,2-benzisothiazolin-3-one.

9. A process as defined in claim 1 wherein the microbiocide is 5-chloro-2-methyl-4-isothiazolin-3-one/2-methyl-4-isothiazolin-3-one.

* * * * *